United States Patent [19]

Drewe et al.

[11] 4,075,002

[45] Feb. 21, 1978

[54] HERBICIDAL COMPOSITIONS HAVING IMPROVED STABILITY

[75] Inventors: Nigel Wyndham Drewe, Maidstone; Roger John Parker, Tonbridge; Tharwat Fouad Tadros, Wokingham, all of England

[73] Assignee: Imperial Chemical Industries Limited, London, England

[21] Appl. No.: 323,396

[22] Filed: Jan. 15, 1973

[30] Foreign Application Priority Data

Jan. 28, 1972 United Kingdom ................. 4042/72

[51] Int. Cl.² .............................................. A01N 9/22
[52] U.S. Cl. ......................................... 71/92; 71/93; 71/94; 71/103; 71/106; 71/118; 71/120; 71/121; 71/DIG. 1

[58] Field of Search ............................. 71/92, DIG. 1

[56] References Cited

U.S. PATENT DOCUMENTS 3,527,593  9/1970  Brian et al. ............................. 71/106

FOREIGN PATENT DOCUMENTS 1,088,981  10/1967  United Kingdom ..................... 71/94
1,088,982  10/1967  United Kingdom ..................... 71/94

*Primary Examiner*—Glennon H. Hollrah
*Attorney, Agent, or Firm*—Cushman, Darby & Cushman

[57] ABSTRACT

Herbicidal compositions are provided which contain a solid herbicide dispersed in an aqueous solution of a herbicidal bipyridylium salt along with a cationic dispersing agent for added stability of the formulation.

8 Claims, No Drawings

HERBICIDAL COMPOSITIONS HAVING IMPROVED STABILITY

This invention relates to herbicidal compositions.

Herbicidal compositions comprising a finely divided insoluble solid herbicide dispersed in an aqueous solution of a herbicidal bipyridylium quaternary salt containing a surface-active agent have been disclosed in British Patent Specification No. 1,088,981. An example of such a composition which has been commercially available comprises a dispersion of diuron in an aqueous solution of paraquat dichloride containing a non-ionic surface active agent sold under the name of Pluronic P75. A difficulty which has been encountered with such compositions is that the particles of the dispersed solid herbicide tend to settle to the bottom of the container and agglomerate together when the composition is stored, particularly when storage takes place at the higher temperatures prevalent in tropical regions. This behaviour is referred to as "claying". The material which has clayed may be very difficult to re-disperse by hand stirring. Another difficulty which is encountered with some compositions is that the dispersed particles of the solid herbicide may flocculate; that is to say, a number of particles cluster together to form loose aggregates referred to as "flocs". These flocs may also be difficult to re-disperse by hand stirring. From a physical chemical point of view these dispersions of solids in solutions of electrolutes are complex systems whose behaviour is difficult if not impossible to predict. After considerable research and experiment, it has now been discovered that compositions having a reduced tendency to clay or flocculate may be obtained by use of a particular group of cationic surface-active agents.

According to the present invention there is provided a herbicidal composition having improved storage characteristics comprising a solid herbicide dispersed in an aqueous solution of a herbicidal bipyridylium quaternary salt, the solid herbicide having an average particle size not exceeding 50 microns, and a dispersing agent which comprises (A) a surface active agent which is (i) a quaternary ammonium salt of the formula:

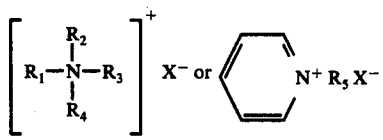

wherein $R_1$ and $R_5$ are aliphatic, preferably alkyl groups of from 8 to 18 carbon atoms and $R_2$, $R_3$ and $R_4$ are aliphatic, preferably alkyl, groups of less than 8 carbon atoms, $R_2$ may also be a benzyl group, and X is an anion; or (ii) a quaternary salt of the formula:

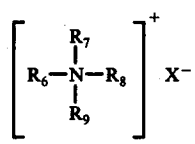

wherein $R_6$ and $R_7$ are aliphatic, preferably alkyl, groups of from 8 to 18 carbon atoms, $R_8$ and $R_9$ are aliphatic, preferably alkyl groups of less than 8 carbon atoms, and X is an anion; or (iii) a quaternary salt of formula:

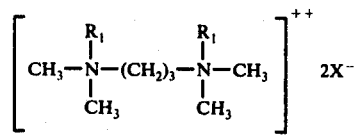

wherein $R_1$ and X are as defined in clause (i) above; or (iv) a quaternary salt of the formula:

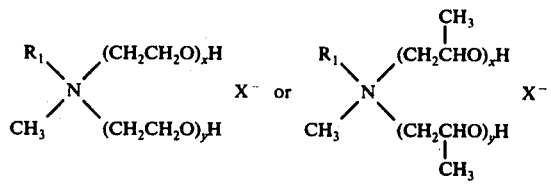

wherein $R_1$ and $X^-$ are defined as in clause 1 above, and x and y each represent an integer from 2 to 23 inclusive; or (v) a quaternary salt of formula:

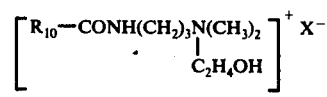

wherein $R_{10}$ is an aliphatic, preferably alkyl, group of 8 to 18 carbon atoms and X is an anion; or (vi) a quaternary salt of formula:

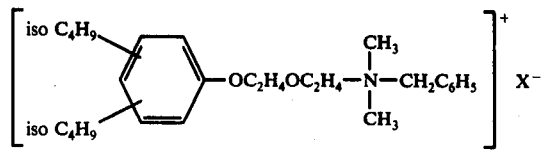

wherein X is an anion, or (B) a surface-active agent which is (i) a acid addition salt of an amine of the formula:

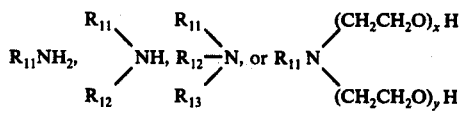

wherein $R_{11}$, $R_{12}$ and $R_{13}$ represent saturated or unsaturated aliphatic groups of from 8 to 18 carbon atoms, or represent mixtures of such saturated or unsaturated aliphatic groups and x and y each represent an integer of from 2 to 23, or (ii) an acid addition salt of a diamine of formula:

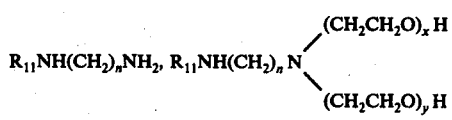

or

-continued

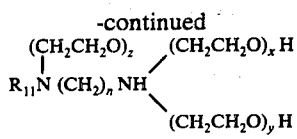

wherein $R_{11}$, $x$ and $y$ are defined as in clause (i) above, $n$ is 2 or 3, and $z$ is an integer of from 2 to 23; or (iii) an acid addition salt of an amine oxide of formula:

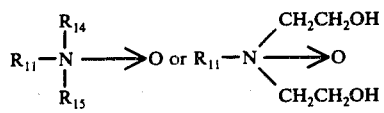

wherein $R_{11}$ is defined as in clause (i) above and $R_{14}$ and $R_{15}$ are aliphatic, preferably alkyl groups, of less than 8 carbon atoms; or (iv) a compound of formula:

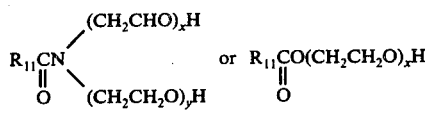

wherein $R_{11}$, $x$ and $y$ are defined as in clause (i) above.

Conveniently, the groups $R_{11}$, $R_{12}$ and $R_{13}$ in the formulae of the surface-active agents of group B above may represent the mixture of aliphatic radicals present in one of the commercially available amines known as coco-amine, soya amine, and tallow amines. These are prepared from the mixtures of fatty acids present in coco oil, soya bean oil and tallow.

Preferably, the quaternary salts and acid addition salts referred to above comprise halides and hydrohalides although other salts for example salts formed from suphuric or nitric acid may be used if desired.

Preferred compositions according to the invention contain at least one surface-active agent selected from group A together with at least one surface active agent from group B above. In some cases, for example, the compositions contain three surface active agents of which one is chosen either from group A or from group B, and the remaining two both from the remaining group.

The concentration of dispersing agent used in the compositions of the invention will depend upon the particular ingredient chosen, but is usually from 10 to 100 grams per liter of the composition and preferably from 20 grams to 60 grams per liter of the composition.

Compositions according to the invention may also comprise further additives such as anti-settling agents and corrosion inhibitors.

Preferred herbicidal bipyridylium quaternary salts are those of the following formulae:

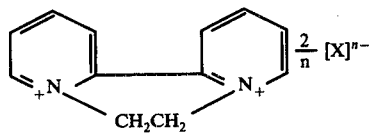

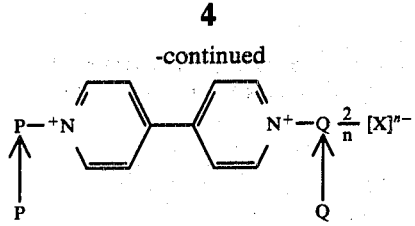

wherein P and Q, which may be the same or different, stand for alkyl radicals of from 1 to 4 carbon atoms which may be substituted by hydroxyl, halogen, carboxyl, alkoxy, alkylcarbonyl, alkoxycarbonyl, carbamoyl or N-substituted carbamoyl: $X^{n-}$ represent an anion and $n$ is an integer from 1 to 4 inclusive.

Particularly preferred herbicidal bipyridylium quaternary salts are those listed below:

1,1'-ethylene-2,'-bipyridylium dibromide (diquat dibromide)
1,1'-dimethyl-4,4'-bipyridylium dichloride (paraquat dichloride)
1,1'-di-2-hydroxyethyl-4,4'-bipyridylium dichloride
1,1'-bis-3,5-dimethylmorpholinocarbonylmethyl-4,4'-bipyridylium dichloride (morfamquat dichloride)
1-(2-hydroxyethyl)-1'-methyl-4,4'-bipyridylium dichloride
1,1'-di-carbamoylmethyl-4,4'-bipyridylium dichloride
1,1'-bis-N,N-dimethylcarbamoylmethyl-4,4'-bipyridylium dichloride
1,1'-bis-N,N-diethylcarbamoylmethyl-4,4'-bipyridylium dichloride
1,1'-di-(piperidinocarbonylmethyl)-4,4'-bipyridylium dichloride
1,1'-diacetonyl-4,4'-bipyridylium dichloride
1,1'-diethoxycarbonylmethyl-4,4'-bipyridylium dibromide The names in brackets alongside some of the compounds in the above list are the accepted common names for the cationic portion of these compounds. Thus "paraquat" is the common name for 1,1'-dimethyl-4,4'-bipyridylium cation. Paraquat is a particularly preferred bipyridylium compound for use in the compositions of the invention. A particularly preferred anion $[X]^{n-}$ is the chloride anion, for reasons of convenience and economy, but any anion which gives rise to a conveniently water-soluble salt may be used if desired. The amount of herbicidal bipyridylium quaternary salt present in the compositions of the invention is preferably from 100 grams to 250 grams per liter calculated on the basis of the cation.

Examples of solid herbicides used in the compositions of the invention include urea herbicides, triazine herbicides and uracil herbicides. Particular examples of these herbicides include the following:

| Urea herbicides | Triazine herbicides |
|---|---|
| monuron | simazine |
| diuron | atrazine |
| neburon | ametryne |
| fluometuron | |
| monolinuron | |
| linuron | |
| Uracial herbicides | |
| bromacil | |
| lenacil | |
| terbacil | |

It is obvious that solid herbicides used in the compositions of the invention must have a melting point which is higher than the temperature at which the composition is to be stored. Preferably the solid herbicide is one having a melting point of at least 100° C As noted above, the compositions may, if desired, also include an anti-settling agent. Examples of anti-settling agents include those sold under the following trade name;

"Santocel" 54 (finely divided Silica)
"Kelzan" DO (Xanthan gum)
"Carbopol" 934 (vinyl polymer with carboxyl groups)
"Alcotex" 88/10 (a polyvinyl alcohol)
Polyvinyl pyrrolidone/"Bentopharm" (pharmaceutical grade bentonite)
"Hydral" (finely divided alumina)

The amount of anti-settling agent used will depend somewhat upon the particular mixture of herbicide being formulated and upon the dispersing agent used, but in general, a concentration of from 0.5% to 5% by weight is suitable.

EXAMPLE 1

This Example illustrates a composition according to the invention comprising diuron dispersed in a solution of paraquat dichloride. The ingredient of the composition are as follows:

| Ingredients | Amount |
| --- | --- |
| Paraquat dichloride | x |
| Technical diuron | y |
| "Duomeen" S | 6.85 |
| Arquad S/50 | 45.60 |
| Concentrated hydrochloric acid | 3.76 |
| Water | to 100 ml. |

In the above table of ingredients, $x$ is the quantity of paraquat chloride solution required to give a final concentration of paraquat cation of 200 grams per liter and $y$ is the amount of diuron required to give a final concentration of 200 grams of diuron per liter.

Duomeen S is a registered Trade Name for a surface active agent of chemical formula: $RNHCH_2CH_2CH_2NH_2$ prepared from the mixture of fatty acids in soya fatty acids. The group R is therefore, derived from the alkyl groups of the mixture of fatty acids in soya fatty acids.

Arquad S/50 is a registered Trade Name for a surface active agent comprising a mixture of quaternary salts of general formula $R\ N\ (CH_3)_3\ Cl^-$ of which the principal constituents are compounds in which R stands for octadecadienyl or octadecenyl. Arquad S/50 is prepared from amines prepared in turn from the mixture of fatty acids present in soya bean oil.

The above composition was prepared by first mixing the diuron with the "Duomeen" S, then wet milling the diuron to produce a finely divided dispersion of diuron in water. The Arquad S/50 was then added and then the paraquate chloride as a solution in water was mixed in.

The composition so obtained did not clay or flocculate on storage for 3 months at 50° C.

EXAMPLE 2

This Example illustrates the preparation of further compositions according to the invention comprising diuron dispersed in an aqueous solution of paraquat chloride. The ingredients of the compositions are set out in the following table.

| Ingredient | Amount, grams/liter | | | |
| --- | --- | --- | --- | --- |
| Paraquat ion | 200 | 200 | 200 | 100 |
| Technical diuron | 200 | 200 | 200 | 300 |
| "Duomeen" S | 29.6 | — | 34.2 | 32.7 |
| Arquad S/50 | — | 61.6 | 15.9 | — |
| Concentrated hydrochloric acid(dl.16) | 16.5 | — | 18.9 | 18.2 |
| Water | to 100 ml | | | |

The compositions containing Arquad S/50 were prepared by first mixing about 20% of the Arquad with the water and diuron, then wet milling the mixture, adding the remaining Arquad S/50 and finally adding the paraquat chloride as a water solution. The compositions set forth in the last foregoing table exhibit excellent storage stability; for example the composition containing 300 grams per liter of diuron shown in the right hand column of the table has stored for 6 months at 50° C completely satisfactorily. Examples of further compositions according to the invention, comprising diuron or another residual herbicide, are given in the table below:

| Ingredient | Quantity in grams | | | |
| --- | --- | --- | --- | --- |
| Paraquat ion | 20 | 20 | 20 | 20 |
| Atrazine | 20 | — | — | — |
| Simazine | — | 20 | — | — |
| Diuron | — | — | 20 | 20 |
| Arquad S/50 | 5.5 | — | 5.4 | — |
| Duomeen S hydrochloride | — | — | — | 4.05 |
| Arquad 16/50 | — | 1.7 | — | — |
| Polyvinyl pyrrolidone | 0.9 | 0.9 | — | — |
| Bentopharm | 2.2 | 2.2 | — | — |
| Water | to 100 ml | | | |

EXAMPLE 3

This Example illustrates compositions according to the invention comprising atrazine dispersed in an aqueous solution of paraquat dichloride. The compositions were prepared by wet milling the atrazine with the surface-active agents to obtain a dispersion of atrazine having an average particle size of less than 50 microns, mixing the dispersion with a solution of paraquat dichloride and diluting with water to the required concentration. Three compositions so prepared are listed in the table below.

| Ingredient | Quantity (grams) in composition No. | | |
| --- | --- | --- | --- |
|  | 1 | 2 | 3 |
| Paraquat ion | 20 | 20 | 20 |
| Atrazine | 20 | 20 | 20 |
| Arquad S/50 | 5.5 | — | — |
| Duomeen S hydrochloride | 1.3 | — | — |
| Polyvinyl-pyrrolidone K15 | — | 0.9 | — |
| Bentopharm | — | 2.2 | — |
| Arquad 16/50 | — | 1.7 | — |
| Ethomeen S hydrochloride | — | 0.6 | — |
| Hyamine 1622 | — | — | 1.5 |
| Aromox DMCD hydrochloride | — | — | 0.8 |
| Arquad 2C75 | — | — | 2.2 |
| Water | to 100 ml. | | |

The above compositions were submitted to storage tests at various temperatures. For comparison, two compositions prepared in the same way as compositions 1 to 3, but using Pluronic P75 as the surface active agent were also submitted to storage tests; in the table below these compositions are numbered 4 and 5. Their ingredients were as follows:

| Ingredient | Amount (grams) in Composition No. | |
|---|---|---|
| | 4 | 5 |
| Paraquat ion | 20 | 20 |
| Atrazine | 20 | 20 |
| Pluronic P 75 | 2.8 | 2.8 |
| Santocel 54 | — | 2.2 |
| Water | to 100 ml | |

The compositions were stored for 14 weeks at various, temperatures and their condition then examined. In the table below, the compositions which were found to have clayed or flocculated are marked by the letter F (failed). Compositions which were satisfactory are marked by the letter S.

| Storage temperature | Composition No. | | | |
|---|---|---|---|---|
| 0° C | 1 | 2 | 4 | 5 |
| 25 | S | S | S | F | F |
| 37 | S | S | S | F | F |
| 50 | S | S | S | F | F |

EXAMPLE 4

This Example illustrates compositions according to the invention comprising a dispersion of simazine in an aqueous solution of paraquat dichloride. The compositions were prepared in the same way as in Example 3 and are listed in the table below.

| Ingredient | Quantity (grams) in composition No. | |
|---|---|---|
| | 1 | 2 |
| Paraquat ion | 20 | 20 |
| Simazine | 20 | 20 |
| Lissolamine A | 1.1 | — |
| Aromox C12 | 0.7 | — |
| Polyvinyl pyrrolidone K15 | 0.9 | — |
| Bentopharm | 2.2 | — |
| Cationic SP | — | 1.6 |
| Ethomid HT15 | — | 0.7 |
| Arquat 2C75 | — | 2.2 |
| Water | to 100 ml | |

For comparison two compositions (3 and 4) containing Pluronic P 75 as the surface active agent were prepared, having the following ingredients.

| Ingredient | Quantity (grams) in composition No. | |
|---|---|---|
| | 3 | 4 |
| Paraquat ion | 20 | 20 |
| Simazine | 20 | 20 |
| Pluronic P75 | 2.8 | 2.8 |
| Santocel 54 | — | 2.2 |
| Water | to 100 ml | |

Storage tests were carried out for 14 weeks as described in Example 3. The results were as follows:

| Storage temperature ° C | Composition No. | | | |
|---|---|---|---|---|
| | 1 | 2 | 3 | 4 |
| 25 | S | S | F | F |
| 37 | S | S | F | F |
| 50 | S | S | F | F |

EXAMPLE 5

This Example illustrates compositions according to the invention comprising terbacil dispersed in an aqueous solution of paraquat dichloride. The compositions were prepared in the same way as those of Example 3.

| Ingredient | Quantity (grams) in composition no. | |
|---|---|---|
| | 1 | 2 |
| Paraquation | 20 | 20 |
| Terbacil | 20 | 20 |
| Arquad 16/50 | 1.7 | 1.7 |
| Ethomeen S25 hydrochloride | 0.6 | 0.6 |
| Polyvinyl-pyrrolidone K15 | 0.9 | — |
| Bentopharm | 2.2 | — |
| Arquad 2C75 | — | 2.2 |
| Water | to 100 ml. | |

For comparison, two compositions (nos 3 and 4) containing Pluronic P75 as the surface-active agent were prepared, having the following ingredients.

| Ingredient | Quantity (grams) in composition No. | |
|---|---|---|
| | 3 | 4 |
| Paraquat ion | 20 | 20 |
| Terbacil | 20 | 20 |
| Pluronic P75 | 2.8 | 2.8 |
| Santocel 54 | — | 2.2 |
| Water | to 100 ml | |

Storage tests were carried out for 14 weeks as described in Example 3; the results are given below:

| Storage Temperature ° C | Composition Nos. | | | |
|---|---|---|---|---|
| | 1 | 2 | 3 | 4 |
| 25 | S | S | F* | F* |
| 37 | S | S | F* | F* |
| 50 | S | S | F* | F* |

*Failed after only 6 weeks

EXAMPLE 6

This Example illustrates a composition (No. 1) according to the invention comprising a dispersion of dinitramine in aqueous paraquat dichloride solution. The composition was prepared as in Example 3.

| Ingredient | Amount (grams) |
|---|---|
| Paraquat ion | 20 |
| Dinitramine | 20 |
| Hyamine 1622 | 1.5 |
| Aromox DMCD hydrochloride | 0.8 |
| Polyvinyl pyrrolidone K15 | 0.9 |
| Bentopharm | 2.2 |
| Water | to 100 ml |

Dinitramine is a residual herbicide having the systematic chemical name: - $N^3,N^3$ diethyl-2,4-dinitro-6-trifluoromethyl-1,3-phenylenediamine.

For comparison, two further compositions (nos. 2 and 3) containing Pluronic P75 were prepared, having the following ingredients:

| Ingredient | Quantity (grams) in composition No. | |
|---|---|---|
| | 2 | 3 |
| Paraquat ion | 20 | 20 |
| Dinitramine | 20 | 20 |
| Pluronic P75 | 2.8 | 2.8 |
| Santocel 54 | — | 2.2 |
| Water | to 100 ml. | |

Storage tests conducted as in Example 3 gave the following results:

| Storage temperature ° C | Composition Nos | | |
|---|---|---|---|
| | 1 | 2 | 3 |
| 25 | S | F | F |
| 37 | S | F* | F |
| 50 | S | F* | F* |

*Failed after only 6 weeks.

EXAMPLE 7

This Example illustrates a composition according to the invention comprising diuron dispersed in an aqueous solution of paraquat dichloride. Three compositions were prepared by the method of Example 3 and are listed in the table below:

| Ingredient | Quantity (grams) in composition No | | |
|---|---|---|---|
| | 1 | 2 | 3 |
| Paraquat ion | 20 | 20 | 20 |
| Diuron | 20 | 20 | 20 |
| Arquad S/50 | 4.0 | — | — |
| Duomeen S hydrochloride | 0.93 | — | — |
| Pluronic P75 | — | 2.8 | 2.8 |
| Santocel 54 | — | — | 2.2 |
| Water | to 100 ml. | | |

Compositions 2 and 3 are for comparison. The compositions were submitted to storage tests for 14 weeks as in Example 3. The results are given in the table below.

| Storage temperature ° C | Composition No. | | |
|---|---|---|---|
| | 1 | 2 | 3 |
| 25 | S | F* | F* |
| 37 | S | F* | F* |
| 50 | S | F* | F* |

(*failed after only 6 weeks)

The following description sets forth the chemical composition of the various substances denoted by the trade names referred to in the specification.

Arquad 16/50

A mixture of quaternary ammonium salts of general formula $RN^+(CH_3)_3Cl^-$ wherein R is 90% hexadecyl 6% octadecyl, and 4% octadecenyl, sold in the form of a 50% w/w solution in a mixture of isopropanol and water containing about 1% of sodium chloride.

Arquad 2C75

A mixture of quaternary ammonium salts of general formula:

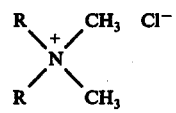

wherein R is 8% octyl, 9% decyl, 47% dodecyl, 18% tetradecyl, 8% hexadecyl, and 10% octadecyl sold as a 75% w/w solution in a mixture of isopropanol and water containing about 0.5% of sodium chloride.

Aromox C12

Bis-2-(hydroxyethyl)cocoamine oxide

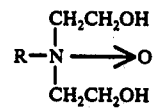

This substance is prepared from cocoamine, which is in turn obtained from the mixture of fatty acids present in coconut oil; the group R therefore represents the mixture of aliphatic radicals present in cocoamine.

Aromox DMCD

Dimethyl cocoamine oxide, having the formula:

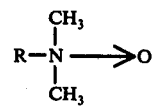

wherein R represents the mixture of aliphatic radical present in the mixture of primary amines comprising cocoamine.

Ethomeen S/25

A soya amine/ethylene oxide condensate of the formula:

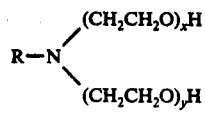

where $x + y = 15$ and R represents the mixture of aliphatic radicals present in the mixture of primary amines comprising soya amine. Soya amine is prepared from the mixture of fatty acids found in soya bean oil.

Ethomid HT/15

A condensate of ethylene oxide with tallow acid amides having the formula:

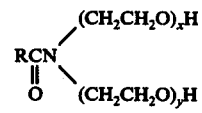

wherein R represents the mixture of aliphatic radicals present in the mixture of aliphatic radicals present in the mixture of fatty acids comprising hydrogenated tallow acid, and $x$ and $y$ total 5.

Hyamine 16

A quaternary salt of formula:

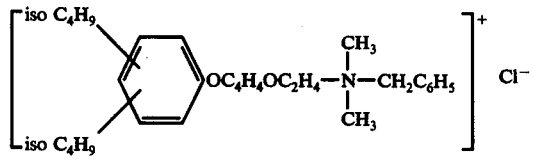

Lissolamine A

A quaternary salt of formula $R\ N^+(CH_3)_3\ Br^-$ wherein R comprises a mixture of alkyl radicals, containing 9.7% hexadecyl, 68% tetradecyl, and 19.9% dodecyl radicals, the residue being alkyl radicals of greater chain length.

Pluronic P75

A block copolymer of polyoxy ethylene oxide and polyoxy propylene of average molecular weight 4100, containing 50% of polyoxy ethylene in the total molecule.

We claim:

1. A herbicidal composition having improved storage characteristics, comprising an effective amount of a solid herbicide dispersed in an aqueous solution of a herbicidal bipyridylium quaternary salt selected from the group consisting of compounds of the formula:

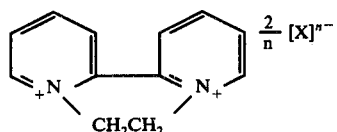

and

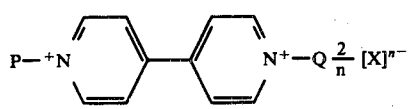

wherein P and Q are selected from the group consisting of alkyl radicals of 1 to 4 carbon atoms and alkyl radicals of 1 to 4 carbon atoms substituted by a radical selected from the group consisting of hydroxyl, halogen, carboxyl, alkoxy, alkylcarbonyl, carbamoyl or N-substituted carbamoyl; $[X]^{n-}$ represents an anion and $n$ is a integer from 1 to 4 inclusive, the solid herbicide having an average particle size not exceeding 50 microns; and a dispersing agent selected from the group consisting of (A)

(i) quaternary ammonium salts of the formula:

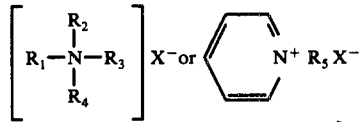

wherein $R_1$ and $R_5$ are aliphatic, preferably alkyl groups of from 8 to 18 carbon atoms and $R_2$, $R_3$ and $R_4$ are aliphatic, preferably alkyl, groups of less than 8 carbon atoms, $R_2$ may also be a benzyl group, and Y is an anion (ii) quaternary salts of the formula:

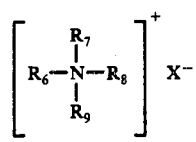

wherein $R_6$ and $R_7$ are aliphatic, preferably alkyl, groups of from 8 to 18 carbon atoms, $R_8$ and $R_9$ are aliphatic, preferably alkyl groups of less than 8 carbon atoms, and X is a anion (iii) quaternary salts of formula:

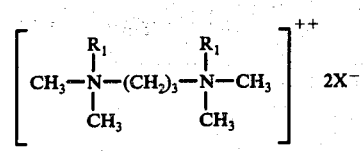

wherein $R_1$ and X are as defined in clause (i) above (iv) quaternary salts of the formula:

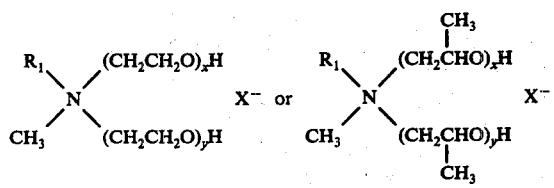

wherein $R_1$ and $X^-$ are defined as in clause 1 above, and $x$ and $y$ each represent an integer from 2 to 23 inclusive;

(v) quaternary salts of formula:

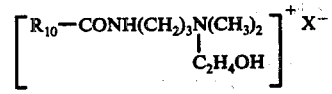

wherein $R_{10}$ is an aliphatic, preferably alkyl group of 8 to 18 carbon atoms and X is an anion;

(vi) quaternary salts of formula:

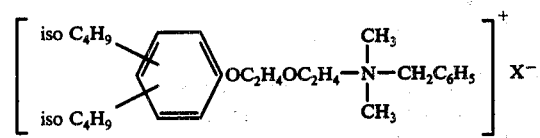

wherein X is an anion; and (B)

(i) acid addition salts of amines of the formula:

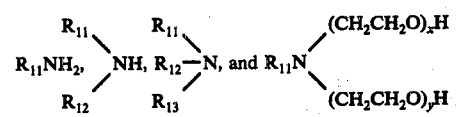

wherein $R_{11}$, $R_{12}$, and $R_{13}$ represent saturated or unsaturated aliphatic groups of from 8 to 18 carbon atoms, or represent mixtures of such saturated or unsaturated aliphatic groups and $x$ and $y$ each represent an integer of from 2 to 23;

(ii) acid addition salts of diamines of formula:

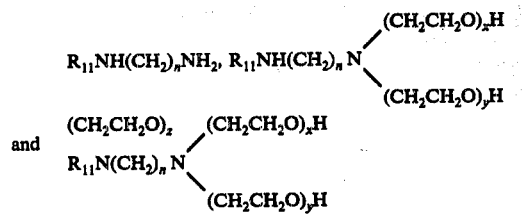

wherein $R_{11}$, $x$ and $y$ are defined as in clause (i) above, $n$ is 2 or 3, and $z$ is an integer of from 2 to 23

(iii) acid addition salts of amine oxides of formula:

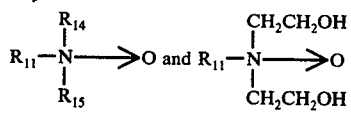

wherein $R_{11}$ is defined as in clause (i) above and $R_{14}$ and $R_{15}$ are aliphatic, preferably alkyl, groups of less than 8 carbon atoms;

(iv) compounds of formula:

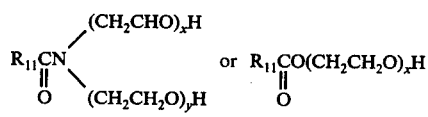

wherein $R_{11}$, $x$ and $y$ are defined as in clause (i) above.

2. A composition according to claim 1 which comprises at least one surface-active agent from Class A and at least one surface-active agent from Class B.

3. A composition according to claim 1 wherein the dispersing agent comprises an acid addition salt of a diamine of formula $RNH(CH_2)_3NH_2$ wherein the group R represents an aliphatic radical of from 8 to 18 carbon atoms.

4. A composition according to claim 1 wherein the concentration of dispersing agent is from 10 to 100 grams per liter of the composition.

5. A composition according to claim 1 wherein the anion $[X]^{n-}$ comprises a chloride, bromide, iodide, methylsulphate, or p-toluenesulphonate ion.

6. A composition according to claim 1 wherein the concentration of herbicidal bipyridylium cation is from 150 to 250 grams per liter of the composition.

7. A composition according to claim 1 wherein the solid herbicide is selected from the group consisting of urea, triazine, uracil, and dinitro-aniline herbicides.

8. A composition according to claim 7 wherein the concentration of the solid herbicide is from 5 grams to 400 grams per liter of the composition.

* * * * *